United States Patent
Blanco (12)

(10) Patent No.: US 6,565,850 B2
(45) Date of Patent: May 20, 2003

(54) HEMORRHOIDAL COMPOSITIONS AND METHOD OF USE

(76) Inventor: Amparo Blanco, Av. Jose Antonio 23.7J.34002, Palencia (ES)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/417,345

(22) Filed: Apr. 5, 1995

(65) Prior Publication Data

US 2003/0035850 A1 Feb. 20, 2003

(51) Int. Cl.⁷ .................. A61K 35/78; A61K 39/385
(52) U.S. Cl. ................ 424/195.1; 514/944; 514/966; 514/882
(58) Field of Search ............... 424/195.1; 514/944, 514/966, 882

(56) References Cited

U.S. PATENT DOCUMENTS

| 4,192,866 A | * | 3/1980 | Anderson | 424/154 |
| 4,383,986 A | * | 5/1983 | Dubash et al. | 424/25 |
| 4,604,384 A |   | 8/1986 | Smith et al. | 514/179 |
| 5,002,675 A |   | 3/1991 | Randisi | 252/49.3 |

FOREIGN PATENT DOCUMENTS

| EP | 0386960 A2 | * | 9/1990 |
| GB | 1261881 |   | 1/1972 |
| JP | 610212515 |   | 9/1986 |
| JP | 620283921 |   | 12/1987 |

* cited by examiner

Primary Examiner—Theodore J. Criares
Assistant Examiner—Jennifer Kim
(74) Attorney, Agent, or Firm—Darby & Darby

(57) ABSTRACT

The present invention is directed to gel compositions useful in the preparation of medicated gel products. Such medicated gel products are suitable for use in the treatment of anorectal disorders such as hemorrhoids. Also disclosed is a method for the treatment of such anorectal disorders using the claimed medicated gel products.

26 Claims, No Drawings

HEMORRHOIDAL COMPOSITIONS AND METHOD OF USE

This invention relates to hemorrhoidal compositions and to a method of treating hemorrhoids and/or diseases of the anorectum using gel compositions. More particularly the invention relates to gel compositions for intrarectal administration in treating hemorrhoids and/or diseases of the anorectum and to processes for preparing said gel compositions.

Hemorrhoids are swollen varicose veins in the mucous membrane inside or just outside the rectum. They can be caused by constipation and the straining associated therewith in passing motions. The excessive pressure involved can cause a fold of the membranous rectal lining to slip down, resulting in a pinching of the veins and subsequent irritation.

Women during pregnancy are also particularly prone to suffer from hemorrhoids because of the pressure in the veins in the abdomen. Other causes include diseases of the digestive tract resulting in anal infection, and cirrhosis of the liver, where obstruction to the blood flow can occur putting increased pressure on the hemorrhoidal veins.

Once formed the hemorrhoids can further deteriorate or rupture when subjected to the additional pressure during bouts of constipation and straining or from external pressure resulting from sitting for any length of time Ruptured and bleeding piles are susceptible to infection and the swelling caused by inflammation can also exacerbate the hemorrhoids by pressing the veins.

It is possible therefore for the hemorrhoidal problems to deteriorate progressively unless effective action is taken.

Treatment methods for hemorrhoids include soothing by immersion in a warm bath, application of ointments and suppositories and surgery to control bleeding and to remove the varicose veins. A combination of such treatments may be employed in treating the disease.

A number of prior art formulations for treating hemorrhoids suggest the possibility of administering in gel form. U.S. Pat. No 4,518,583 describes a composition comprising urea, hydrogen peroxide or benzoyl peroxide, an anaesthetic and a vehicle based on a viscous solution of polyvinylpyrrolidine in glycerine. U.S. Pat. No. 4,945,084 teaches the addition of sucralfate to hemorrhoidal compositions and illustrates a gel formulation based on Samuet. No humectant or lubricant is present. EP Publication No 225832 describes a composition in gel form containing a silica gelling agent and a vegetable oil of natural origin which has been hyperoxygenated. U.S. Pat. No. 4,518,583 teaches a composition which can be in gel form for use in treating hemorrhoids and anorectal diseases comprising a peroxide and containing glycerine as humectant, emollient and lubricant.

Currently marketed topical hemorrhoidal compositions are either ointments or suppositories for application directly to the affected part or region of the body. Such compositions are generally based on a carrier comprising one or more fatty, oily or greasy components which are used to impart lubricating properties to the composition and thereby facilitate the administration of the composition by the user. The aim of such treatment is to provide the user with varying degrees of symptomatic relief in particular before and during defecation.

One of the main disadvantages of compositions based on fatty, greasy or oily components as carriers is the staining or soiling of clothing which can accompany their use. Aqueous compositions on the other hand are easier to remove from clothing. Additionally where greasy compositions are applied to affected parts by hand, users can experience added difficulties in washing their hands scrupulously clean. Yet a further disadvantage is that hydrophilic drugs are insoluble or of low solubility in fatty, oily or greasy carriers and therefore drug absorption from such compositions may be poor.

While there is a need for a hemorrhoidal carrier with satisfactory lubricant properties while possessing reduced stain or soiling properties and providing improved drug bioavailability.

It has surprisingly been found that a gel based on a water soluble cellulose derivative as gelling agent, propylene glycol as humectant and water in defined ranges possesses excellent lubricating properties and water-retaining properties such as to provide effective symptomatic relief for hemorrhoid sufferers. Such an aqueous gel base is also particularly compatible with ionic active ingredients. Further advantages of said gel base are that it avoids oily, greasy and fatty components, it is water miscible, and it is clear thereby avoiding staining or soiling of clothing. It can also be easily washed from the users hands. The combination of gelling agent and humectant also provides excellent water retaining properties after applying to the anus thereby giving a long term lubricating effect up to and during defecation. Yet a further advantage is that the large water content has a cooling and soothing effect on the user giving improved symptomatic relief.

In a first aspect, this invention provides use of an aqueous gel composition which contains one or more drugs effective in treating hemorrhoids and a carrier comprising a water soluble cellulose derivative as gelling agent in an amount from about 0.2% to about 10% by weight of the total composition, propylene glycol in an amount of from about 5% to about 45% by weight of the total composition and water in an amount up to about 94% by weight of the total composition.

This invention also provides a method of treating hemorrhoids in a human so afflicted which comprises administering intrarectally and/or to the anorectal region an aqueous gel composition which contains one or more drugs effective in such treatment and a carrier comprising a water soluble cellulose derivative as gelling agent in an amount from about 0.2% to about 10% by weight of the total composition, propylene glycol in an amount of from about 5% to about 45% by weight of the total composition and water in an amount up to about 94% by weight of the total composition.

In a further aspect, this invention provides an aqueous gel composition for intrarectal administration in the treatment of hemorrhoids and/or in the treatment of anorectal disease which contains one or more drugs effective in such treatment excluding topical corticosteroids and a carrier comprising a water soluble cellulose derivative as gelling agent in an amount from about 0.2% to about 10% by weight of the total composition, propylene glycol in an amount of from about 5% to about 45% by weight of the total composition and water in an amount up to about 94% by weight of the total composition.

To provide optimum lubricating and dispensing properties, it is preferred that the ratio of the cellulose derivative and the humectant to water are such that a gel has the viscosity from about 25000 cps to about 150000 cps @20° C. (as measured using spindle S96 @10 rpm on a Brookfield DVII+). Preferably the viscosity is in the range 40,000 to 100,000 cps @20° C.

In a preferred embodiment the gel formulation comprises from about 0.5 to about 5% by total weight of water soluble cellulose derivative, preferably about 1 to about 4%, most preferably about 2% by weight. Examples of cellulose derivatives useful as gelling agents are hydroxyethylcellulose, hydroxypropylmethylcellulose, methyl cellulose, methylhydroxyethylcellulose, methylhydroxypropylcellulose and carboxymethylcellulose and combinations thereof. The preferred gelling agent is hydroxyethylcellulose.

Also preferred are compositions comprising propylene glycol in an amount from about 10 to about 30% by weight, preferably about 12 to about 18% by weight, most preferably about 15% by weight.

The water present in the formulation advantageously provides a cooling effect in use and can be adjusted relative to the amounts of the other ingredients especially the gelling agent to give a satisfactory viscosity to the gel. It is preferred that the viscosity is high enough so that the gel is not too mobile and so is retained in the anus when applied thereto, yet low enough so that the gel can be dispensed satisfactorily from a tube or other dispenser. A further advantage of a water based gel is that dispensers may be cold-filled unlike grease based ointments which are generally hot filled to achieve a lower viscosity so that the tubes may be filled prior to cooling.

To achieve the desired water content, the water may be incorporated by adding some or all in the form of hamamelis water. Hamamelis water is a clear colorless liquid with astringent properties. Astringents are effective when applied to the skin or mucous membranes for a local and limited effect. Astringents coagulate the protein in the skin cells, thereby protecting the underlying tissue and decreasing the cell volume. When appropriately used, astringents lessen mucous and other secretions and help relieve local anorectal irritation and inflammation.

Hamamelis water in a concentration of 10–50% is recommended as an astringent for external use in anorectal disorders. Hamamelis water is prepared by macerating recently cut and partially dried dormant twigs of *Hamamelis virginiana* L in water, distilling and adding the requisite quantity of ethanol to the distillate, e.g. about 13 to 15% v/v. Typical quantities of hamamelis water used in the compositions of this invention comprise from about 10 to about 60% by weight of the total composition, e.g. 35–55%, preferably about 50% by weight. Additional water may be added to adjust the viscosity to that desired. Accordingly hamamelis water functions both as a source of one or the active ingredient for the composition (i.e. an astringent) and also for providing some or all of the water content. Ethanol is present in the hamamelis water and may therefore be another constituent of the formulations of this invention. The presence of ethanol also enhances the solubility of the active constituents and may comprise 0 to about 10% by weight of the total composition.

Other ingredients and active constituents may be incorporated in the gel composition of this invention especially other astringents, vasoconstrictors, topical steroidal anti-inflammatories, such as hydrocortisone, and/or local anaesthetics to provide symptomatic relief and/or ameliorate the pain accompanying defecation. Preferably such active ingredients are water soluble (e.g. ionic) in which case the carrier base allows a faster onset of action because the actives are held in solution. The viscous properties of the gel also minimise physical risk of loss due to run out.

Examples of astringents that may be used are zinc oxide and calamine. However hamamelis water is particularly preferred as astringent since being a solution it is particularly suited to, and mutually compatible with, the hydrophilic carrier base of this invention. It is especially preferred that the ingredients and active constituents are colourless and for this reason hamamelis water is also particularly preferred since it provides a clear formulation. Crystal clear formulations which are provided by this invention are also very much preferred because the clarity of the gel is perceived by the user as depicting cleanliness thereby optimising user confidence and user compliance.

Examples of vasoconstrictors that can be used are phenylephrine hydrochloride, ephedrine sulphate, epinephrine and epinephrine hydrochloride. The preferred vasoconstrictor is phenylephrine hydrochloride in an amount up to about 0.35% w/w of the total composition, e.g. about 0.1 to about 0.3%, preferably about 0.25%.

Phenylephrine HCl is believed to relieve itching caused by histamine release and reduces congestion in the anorectal area. It acts primarily on the alpha-adrenergic receptors and produces vasoconstriction by a direct effect on receptors rather than by norephinephrine displacement. Recommended dosage is 0.25% applied up to 4 times a day. When phenylephrine is used we have found it particularly advantageous for stability to incorporate an antioxidant system in the formulation.

Local anaesthetics that can be incorporated as active ingredients in the compositions of this invention include benzocaine (e.g. 5 to 20% by weight) benzyl alcohol (e.g. 1 to 4% by weight); dibucaine (HCl) (e.g. 0.25 to 1% by weight); lidocaine e.g. (0.5 to 5% by weight); pramoxine hydrochloride (e.g. about 1% by weight) and tetracaine (HCl) e.g. 0.5 to 1% by weight).

In a further aspect this invention provides a composition for treating hemorrhoids consisting essentially of hamamelis water up to about 50% by weight of total composition; propylene glycol from about 10 to about 20% by weight of composition; hydroxethylcellulose from about 1 to about 2.5% by weight, and water qs 100 per cent by weight. Phenylephrine hydrochloride may also be present in an amount from about 0.2 to 0.3% by weight.

The composition of the invention may also comprise further excipients including antioxidants and preservatives as required. When phenylephrine HCl is used as an active ingredient preferred antioxidants are sodium citrate (0.3 to 20%), sodium metabisulphite(0.01–1%) and disodium edetate (0.005 to 0.1%) where the figures in brackets show the preferred concentrations. Preservatives that can be used include methyl and/or propyl p-hydroxybenzoate.

In an especially preferred aspect this invention provides a topical hemorrhoidal composition as herein described in the form of an aqueous clear gel incorporating one or more soluble actives.

The compositions of this invention may be prepared by mixing the ingredients in any convenient order and allowing a gel to form. In a preferred sequence, the compositions of this invention may be prepared by dispersing the water soluble cellulose derivative in a portion e.g about ⅔ of the propylene glycol and adding to the water constituents comprising hamamelis water if required and any further active drug component and the remainder of the propylene glycol. The resulting mixture is stirred until a gel is formed, e.g for up to 1 hour.

EXAMPLE 1

Gel compositions of the present invention based on hamamelis water and phenylephrine hydrochloride as actives are prepared by the following general procedure:

Any salts to be incorporated (phenylephrine hydrochloride, sodium citrate, sodium metabisulphite, disodium edetate) are dissolved in hamamelis water and deionised water to give a clear solution. Methyl and propyl p-hydroxybenzoates are dissolved in approximately one third of the amount of propylene glycol to be used and added to the salt solution. The water soluble cellulose derivative (hydroxyethylcellulose) is dispersed in the remaining (approximately two thirds) propylene glycol and added to the salt/p-hydroxybenzoate solution. The resulting mixture is stirred and homogenised in a jacketed Giusti vessel until a clear homogenous gel is formed. No heating is necessary during the manufacture and therefore all steps can be carried out at ambient temperature.

The following clear gel formulations are prepared according to the above procedure:

|  | FORMULATION NO | | | | |
|---|---|---|---|---|---|
|  | 1 | 2 | 3 | 4 | 5 |
| INGREDIENT | % w/w | % w/w | % w/w | % w/w | % w/w |
| Hydroxyethylcellulose | 1.75 | 2.00 | 2.25 | 1.50 | 2.0 |
| Propylene glycol | 15 | 15 | 20 | 12 | 12 |
| Phenylephrine HCl | — | 0.25 | 0.25 | 0.25 | — |
| Sodium citrate | — | 0.30 | 0.30 | 0.30 | — |
| Sodium metabisulphite | — | 0.50 | 0.50 | 0.50 | — |
| Disodium edetate | — | 0.10 | 0.10 | 0.10 | — |
| Methyl p-hydroxybenzoate | 0.20 | 0.20 | 0.20 | 0.20 | 0.20 |
| Propyl p-hydroxybenzoate | 0.05 | 0.05 | 0.05 | 0.05 | 0.05 |
| Hamamelis water | 50 | 50 | 50 | 50 | 50 |
| Deionised water | 33.0 | 31.60 | 26.35 | 35.10 | 35.75 |
|  | 100% | 100% | 100% | 100% | 100% | b) In the case of Formulation No 2 the amounts shown below were used to produce a 50 kg batch.

| Natrosol (250 HHX-Pharm) | 1.000 kg |
|---|---|
| Propylene glycol | 7.500 kg |
| Phenylephrine HCl | 0.125 kg |
| Sodium citrate | 0.150 kg |
| Sodium metabisulphite | 0.250 kg |
| Disodium edetate | 0.050 kg |
| Methyl p-hydroxybenzoate | 0.100 kg |
| Propyl p-hydroxybenzoate | 0.025 kg |
| Distilled witch hazel | 25.000 kg |
| Deionised distilled water | 15.800 kg |
|  | 50.000 kg |

The manufacturing process was as follows:

1. It was ensured that the working area and equipment were clean. A 50 liter Giusti Pharmix mixer (J.11544B) vessel was wiped down inside with clean cloth impregnated with 70% ethanol solution.
2. 25.0 kg Distilled witch hazel (hamamelis water) and 15.8 kg deionised water were placed into the Giusti vessel. The initial temperature was recorded.
3. 0.125 kg Phenylephrine HCl, 0.150 kg sodium citrate, 0.05 kg disodium edetate, 0.25 kg sodium metabisulphite were added into the Giusti vessel and stirred with contra-rotating stirrers and emulsifier. Stirring time: 25 minutes. Contra-rotating stirrer speed: Inner at 14 rpm; Outer at 30 rpm. Emulsifier speed: Slow (1400 rpm).
4. Into a separate stainless steel vessel 0.10 kg methyl p-hydroxybenzoate and 0.025 kg propyl p-hydroxybenzoate were added to 2.5 kg propylene glycol using a propeller stirrer (Ika-Labortechnik RW20DZM) (at 250 rpm) fitted with a 10 cm squared paddle until dissolved. Stirring speed: 250 rpm. Stirring time 20 minutes.
5. The solution from step 4 was added to the Giusti vessel and stirred with the contra-rotating stirrer and emulsifier. Stirring time: 20 minutes. Contra-rotating stirrer speed: Inner at 14 rpm; Outer at 30 rpm. Emulsifier speed: Slow (1400 rpm).
6. To the same stainless steel vessel from step 4, 5.0 kg propylene glycol was added and while stirring with propeller stirrer, 1 kg hydroxyethyl cellulose (Natrosol 250 HHX-Pharm., as supplied by Aqualon Ltd) was added slowly until fully dispersed. Stirring time: 20 minutes. Stirring speed: 250 rpm
7. The dispersion from step 5 was poured very slowly into the Giusti Vessel and stirred with contra-rotating stirrer and emulsifier.
8. The product was stirred under vacuum using the outer stirrer only to de-aerate the product. The final temperature was recorded. Stirring time: 30 minutes. Outer stirrer speed: 30 rpm. Pressure: −1 bar.
9. The product was transferred to a stainless steel vessel prior to packaging in 25 g and 50 g tubes.

The formulations had the following physical properties:

pH: 6.07

Viscosity: 43,500 cps

Density: 1.014 g/cm$^3$

Appearance: Clear gel

EXAMPLE 2

Gel formulations 6 and 7 below (laboratory scale) were prepared based on the following:

Gelling system: Natrosol (250 HHX-Pharm) (hydroxyethylcellulose)

Anti-oxidant/Chelating system: Sodium citrate Sodium metabisulphite Disodium edetate Preservative system: Methyl p-hydroxybenzoate Propyl p-hydroxybenzoate Actives: Hamamelis water (distilled witch hazel) and phenylephrine HCl.

a) Formulation 6

The % amounts used were as follows:

|  | Materials | Formulation 6 % w/w |
|---|---|---|
| A | Natrosol (hydroxyethylcellulose) | 1.75 |
|  | Propylene glycol | 10.00 |
| B | Phenylephrine HCl | 0.25 |
|  | Na citrate | 0.30 |
|  | Na metabisulphite | 0.50 |
|  | Disodium edetate | 0.10 |
| C | Methyl p-hydroxybenzoate | 0.20 |
|  | Propyl p-hydroxybenzoate | 0.05 |
|  | Propylene glycol | 5.00 |
| D | Distilled witch hazel | 50.00 |
|  | DI distilled water | to 100.00 |

The method used was as set out in Example 1, i.e:

Dissolve B in D. Set aside

Dissolve methyl and propyl p-hydroxybenzoates in one third of the propylene glycol until dissolved (stirring approximately 30 mins.)

Add C to B+D

Predisperse Natrosol in propylene glycol. Add to (B+D+C) solution.

Leave stirring till a clear gel is formed (approximately 1 hour)

b) Formulation 7

A similar formulation was prepared using the following amounts:

| Material | Formulation 7 Amount (g) |
|---|---|
| Natrosol (hydroxyethylcellulose) | 17.49 g |
| Propylene glycol | 150.00 g |
| Methyl p-hydroxybenzoate | 2.00 g |
| Propyl p-hydroxybenzoate | 0.51 g |
| Phenylephrine HCl | 17.49 g |
| Sodium citrate | 3.00 g |
| Disodium edetate | 1.00 g |
| Sodium metabisulphite | 5.00 g |
| Hamamelis water | 500.00 g |
| Distilled water | 318.51 g |

In both cases gels were obtained with the following physical properties:

| | pH | Viscosity (cps) @ 10 rpm/S96 | Colour |
|---|---|---|---|
| Formulation 6 | 5.50 | 66,000 | Transparent |
| Formulation 7 | 6.05 | 48,000 | Transparent |

Viscosity was measured using a Brookfield Viscometer Model DVII+ using an S96 spindle and a spin rate of 10 revolutions per minute at 20° C.

Viscosity and pH values were acceptable for a topical gel formulation.

EXAMPLE 3

This example illustrates the large scale (50 kg) preparation of a clear topical gel formulation of this invention.

The manufacturing method used is summarised below:

Step 1 Distilled Witch Hazel and distilled water were placed into a 75 liter Giusti vessel.

Step 2 Phenylephrine HCl, sodium citrate, EDTA, sodium metabisulphite were added to the Giusti vessel and stirred @30 rpm and emulsified @ slow speed (1400 rpm) for 25 minutes.

Step 3 Methyl and propyl p-hydroxybenzoates were dissolved in 1/3 of the total propylene glycol using a separate steel vessel and agitator (Ika-Labortechnik RW20DZM) with squared paddle for 30 minutes.

Step 4 Solution from Step 3 was added to Giusti vessel and stirred @25 rpm and emulsified @slow speed 1400 rpm for 20 minutes.

Step 5 In same steel vessel as used above Natrosol was dispersed in the remainder of the propylene glycol (2/3 of the total content) using the previous agitator and paddle for 20 minutes.

Step 6 Dispersion from Step 5 was poured slowly in to the Giusti Vessel and stirred @30 rpm and emulsified @ slow speed 1400 rpm for 30 minutes. The product was de-aerated at 1 bar negative pressure.

The following quantities were used:

| | |
|---|---|
| Natrosol (250 HHX-Pharm) | 0.875 kg |
| Propylene glycol | 7.500 kg |
| Methyl p-hydroxybenzoate | 0.100 kg |
| Propyl p-hydroxybenzoate | 0.025 kg |
| Phenylephrine HCl | 0.125 kg |
| Sodium citrate | 0.150 kg |
| Disodium edetate | 0.050 kg |
| Sodium metabisulphite | 0.250 kg |
| Hamamelis water | 25.000 kg |
| Distilled water | 15.925 kg |

Physical characteristics for the large scale batch were measured as follows:

DENSITY (Paar DMA 38 Density Meter)

Measuring the density of 2 samples at 20° C.

Results: a) 1.0143 g/cm
b) 1.0144 g/cm pH Measurements (Laboratory pH meter PHM 92)

Measuring the pH values in 2 samples at 20° C.

Results: a) 6.07
b) 6.06

Viscosity Measurements

Measuring viscosity of 2 samples using a Brookfield DVII+ Viscometer (Set up in spindle S96, 10 RPM at 20° C.)

Results: a) 39 000 cps
b) 40 000 cps

Formulations according to the above Examples are packaged in tubes each with an applicator adapted for intrarectal administration. Alternatively the flow properties of the formulations allow administration to be carried out by hand.

COMPARATIVE EXAMPLES a) The suitability of Lubrajel (described below) as a gel forming agent was investigated in the Example below. Lubrajel has the following physical properties:

| | |
|---|---|
| Form | Viscous gel |
| Colour | Clear, colourless |
| pH | 5.0–6.0 (typical) |
| Flash point | non-flammable |
| Solubility in water | complete |

Lubrajel can be described as a hydrated polymeric complex, the water of hydration of which is subject to change with the humidity of the atmosphere to which it is exposed. It is a clathrate formed by the reaction of sodium glycerate with a methacrylic acid polymer, stabilized with a small amount of propylene glycol, followed by controlled hydration of the resultant product. This glycerate polyhydrate complex is remarkably stable, releasing its combined water only with difficulty.

The addition of small amounts of methyl and propyl p-hydroxybenzoates helps control microbial growth.

Lubrajel is characterised by its non-allergenic properties and its excellent moisturising qualities. It is used as a vaginal lubricant and as a lubricant in endoscopy and hence was expected to produce a satisfactory vehicle.

The suitability of Lubrajel in producing a hemorrhoidal gel formulation was examined as follows:

1. Lubrajel MS showed a viscosity of >99×10$^3$ cps @10 rpm/S96. When diluted with water up to 40% w/w the mixture had an acceptable texture and viscosity (ca. 80×10³ cps @10 rpm/S96).

2. To the previous gel 0.25% w/w phenylephrine HCl powder was added.
Result: Viscosity ca. 26×10³ cps @10 rpm/S96

The addition of a salt caused a marked decrease in viscosity indicating ionic materials apparently destroy the clathrate structure.

The viscosity value and texture for this topical formulation were unacceptable.

3. Addition of:
0.25% w/w phenylephrine HCl
0.3% w/w Na citrate
0.5% w/w Na metabisulphite
0.1% w/w disodium edetate to Lubrajel MS
Result: Viscosity ~17×10³ cps @10 rpm/S96

The addition of salts as powders broke the Lubrajel structure decreasing viscosity remarkably.

The viscosity value and texture for this topical formulation were unacceptable.

4. Pre-dissolved phenylephrine HCl in water to final concentration of 50% w/w Lubrajel MS, 0.25% w/w phenylephrine HCl.
Result: Viscosity ~30×10³ cps @10 rpm/S96 b) A Carbopol gel was formed containing phenylephrine as active. The resulting gel was found to be very watery and non-lubricating.

The excellent lubricating properties of the formulation of this invention were demonstrated by comparative test described below.

LUBRICITY STUDY

A lubricity test was performed comparing lubricity of Lubrajel MS (viscosity 80,000 cps) from step 1 above with the Natrosol formulation described in Example 2 above (viscosity 66,000).

In this test 15 people were asked to apply the formulations to their fingers and report which gel had a more lubricating feel, giving a greasier sensation. Thirteen answered that the Natrosol gel of Example 2 felt more lubricating whereas only one answered in favour of the Lubrajel MS gel of step 1 and one expressed no preference.

What is claimed is:

1. A method of treating hemorrhoid and/or anorectal disorders in a human so afflicted, which method comprises administering intrarectally and/or to the anorectal region an aqueous gel composition effective in treating hemorrhoids consisting essentially of hamamelis water up to about 50% and a carrier comprising (i) a gelling agent consisting of one or more water soluble cellulose derivatives in an amount from about 0.2% to about 10% by weight of the total composition, (ii) propylene glycol in the amount of from about 5% to about 45% by weight of the total composition and (iii) water in an amount up to about 94% by weight of the total composition, which aqueous gel composition avoids oily, greasy or fatty components.

2. A method of treating hemorrhoid disorders in a human so afflicted which method compromises administering intrarectally and/or to the anorectal region an aqueous gel composition effective in treating hemorrhoids consisting of hamamelis water up to about 50% and a carrier comprising (i) a gelling agent consisting of one or more water soluble cellulose derivatives in an amount from about 0.2% to about 10% by weight of the total composition, (ii) propylene glycol in the amount of from about 5% to about 45% by weight of the total composition, and (iii) water in an amount up to about 94% by weight of the total composition, which aqueous gel composition avoids oily, greasy or fatty components.

3. The method of claim 1 wherein the hamamelis water is present in an amount from of about 10% to about 50% by weight of the total composition.

4. The method of claim 3 wherein the hamamelis water is present in an amount of about 50% by weight of the total composition.

5. The method of claim 1 wherein the cellulose derivative is selected from the group consisting of hydroxyethylcellulose, hydroxypropylmethylecellulose, methyl cellulose, methylhydroxyethylcellulose, methylhydroxypropylcelulose, carboxymethyl cellulose and a combination thereof.

6. The method of claim 1 wherein the cellulose derivative is hydroxyothylcellulose.

7. The method of claim 1 wherein the cellulose derivative is present in an amount from about 0.5 to about 5% by weight of the total composition.

8. The method of claim 1 wherein the propylene glycol is present in an amount from about 10% to about 20% by weight of the total composition.

9. The method of claim 1 wherein the composition has a viscosity from about 25000 cps to about 150000 cps at 20° C.

10. A method of treating hemorrhoids in a human so afflicted, which method comprises administering intrarectally and/or to the anorectal region an aqueous gel composition consisting essentially of hamamelis water up to about 50% by weight of total composition: and a carrier consisting essentially of (i) propylene glycol from about 10% to about 20% by weight of the composition, (ii) hydroxyethylcellulose from about 1 to about 2.5% by weight, and (iii) water qs 100 percent by weight, which aqueous gel composition avoids oily, greasy or fatty components.

11. A method of treating hemorrhoids in a human so afflicted, which method comprises administering intrarectally and/or to the anorectal region an aqueous gel composition consisting essentially of hamamelis water up b about 50% by weight of total composition; phenylephrine hydrochloride in an amount from about 0.2 to 0.3% by weight; and a carrier comprising (i) propylene glycol from about 10% to about 18% by weight of the composition, (ii) hydroxyethylcellulose from about 1 to about 3% by weight, and distilled water qs 100 per cent by weight, wherein the aqueous gel composition avoids oily, greasy or fatty components.

12. An aqueous gel composition for intrarectal administration in the treatment of hemorrhoids and/or In the treatment of anorectal disease consisting essentially of hamamelis water up to about 50% and a carrier comprising (i) a gelling agent consisting of one or more water soluble cellulose derivatives in an amount from about 0.2% to 10% by weight of the total composition, (ii) propylene glycol in an amount of from about 5% to about 45% by weight of the total composition, and (iii) water in an amount up to about 94% by weight of the total composition, which aqueous gel composition avoids oily, greasy and fatty components.

13. The composition of claim 12 wherein the hamamelis water is present in an amount from about 10% to about 60% by weight of the total composition.

14. The composition of claim 13 wherein the hamamelis water is present in an amount of about 50% by weight of the total composition.

15. The composition of claim 12 wherein the cellulose derivative is selected from the group consisting of hydroxyethylcellulose, hydroxypropylmethylecellulose, methyl cellulose, methylhydroxyethylcellulose, methylhydroxypropylcelulose, carboxymethylcellulose, and combinations thereof.

16. The composition of claim 12 wherein the cellulose derivative is hydroxyethylcellulose.

17. The composition of claim 16 wherein the cellulose derivative is present in an amount from about 0.5% to about 5% by weight of the total composition.

18. The composition of claim 12 wherein the propylene glycol is present in an amount from about 10% to about 20% by weight of the total composition.

19. The composition of claim 12 having a viscosity from about 25000 cps to about 150000 cps at 20° C.

20. A composition for treating hemorrhoids consisting essentially of hamamelis water up to about 50% by weight of total composition; propylene glycol from about 10 to about 20% by weight of the composition; hydroxyethylcellulose from about 1 to about 2.5% by weight, and water qs 100 per cent by weight, which aqueous gel composition avoids oil, greasy or fatty components.

21. A composition for treating hemorrhoids consisting essentially of hamamelis water in an amount up to about 50% by weight of total composition; propylene glycol from about 10% to about 18% by weight of the composition; hydroxyethylcellulose from about 1% to about 3% by weight; phenylephrine hydrochloride in an amount from about 0.2% to 0.3% by weight; and distilled water qs 100 per cent by weight.

22. The composition of claim 12 wherein the cellulose derivative is present in an amount from about 0.5% to about 5% by weight of the total composition.

23. The composition of claim 12 wherein the propylene glycol is present in an amount from about 10% to about 20% by weight of the total composition.

24. The composition of claim 12 having a viscosity from about 25000 cps to about 150000 cps at 20° C.

25. A composition for treating hemorrhoids consisting essentially of hamamelis water up to about 50% by weight of total composition; propylene glycol from about 10 to about 20% by weight of the composition; hydroxyethylcellulose from about 1 to about 2.5% by weight, and water qs 100 per cent by weight, which aqueous gel composition avoids oily, greasy or fatty components.

26. A composition for treating hemorrhoids consisting essentially of hamamelis water in an amount about 50% by weight of total composition; propylene glycol from about 10% to about 18% by weight of the composition; hydoxyethylcellulose from about 1% to about 3% by weight; phenylephrine hydrochloride in an amount from about 0.2% to 0.3% by weight; and (distilled water qs 100 per cent by weight, which aqueous gel composition avoids oily, greasy or fatty components.

* * * * *